United States Patent [19]

Beazley

[11] 4,416,627
[45] Nov. 22, 1983

[54] ORTHODONTIC APPLIANCE

[76] Inventor: William W. Beazley, 3055 El Vido, Los Angeles, Calif. 90049

[21] Appl. No.: 804,345

[22] Filed: Jun. 7, 1977

[51] Int. Cl.³ ................................................ A61C 3/00
[52] U.S. Cl. ......................................... 433/18; 433/8; 433/17; 433/22
[58] Field of Search ..................... 32/14 A; 433/8, 17, 433/18, 22

[56] References Cited

U.S. PATENT DOCUMENTS

| 274,367 | 3/1883 | Patrick | 32/14 A |
|---|---|---|---|
| 3,237,305 | 3/1966 | Hegedus | 32/14 A |
| 3,654,702 | 4/1972 | Kelly, Jr. | 32/14 A |
| 3,925,893 | 12/1975 | Anderson | 32/14 A |

*Primary Examiner*—John J. Wilson
*Attorney, Agent, or Firm*—Ralf H. Siegemund

[57] ABSTRACT

The orthodontic appliance includes the usual band fitted around the tooth, a pair of T-shaped brackets with an aligned groove for placing the arch wire; a ligating element having a flat base and a button on top is placed on the brackets to hold the arch wire; the ligating element is fastened to the brackets by means of wires welded to the bottom of the ligating element; an elastic band can be fastened to the button as well as to the button on a ligating element analogously tied to another tooth.

4 Claims, 6 Drawing Figures

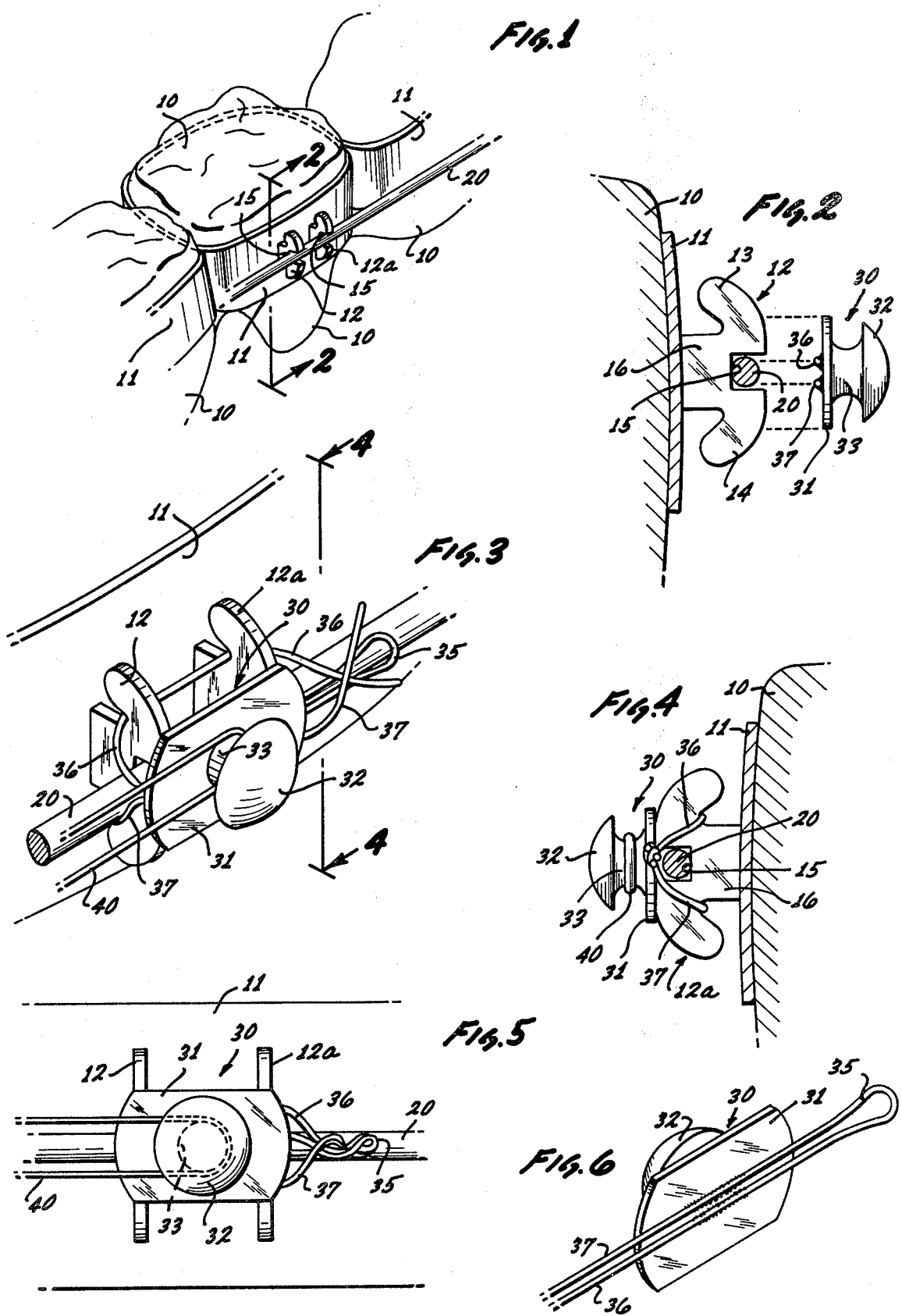

ORTHODONTIC APPLIANCE

BACKGROUND OF THE INVENTION

The present invention relates to an orthodontic appliance for use with an orthodontic arch wire.

Generally speaking, orthodontics involves the straightening of teeth. It is common practice here to fit each tooth of a row of teeth with a metal band and to provide some kind of bracket, clamp, clip or the like on each of the bands. A so-called arch wire is strung across the bands engaging the respective brackets, clamps, etc. for being held and positioned therewith. The ends of the arch wires are tied in some fashion to the molars. Typical devices and appliances of this type are disclosed, for example, in U.S. Pat. Nos. 1,553,797; 1,594,144; 2,767,469; 3,292,260; and 3,871,096.

Another type of orthodontic procedure involves also metal bands fitted around two particular teeth, and an elastic band is strung between suitable fasteners on the bands. Devices of this type are disclosed, for example, in U.S. Pat. No. 3,905,111 or U.S. Pat. No. 3,925,893.

Practicable appliances or devices suitable for both types of orthodontic procedures are not available at the present time, but it is frequently desirable to provide for both types of procedures at the same time. The problem is that the two types of fasteners on the bands interfere with each other in most instances. Moreover, there is a fundamental conflict in the two procedures in that teeth straightening by means of an arch wire requires fastening the arch wire to each and every tooth of a row, whereas teeth straightening by means of elastic bands involves selected teeth only and different pairs at different times.

SUMMARY OF THE INVENTION

It is an object of the present invention to provide a new and improved orthodontic appliance which combines the function of elastic band anchoring with arch wire fastening and positioning.

In accordance with the preferred embodiment of the invention, it is suggested to use two T-shaped brackets on each band being fitted around a tooth, which brackets have two aligned grooves or channels receiving the arch wire. A ligating element in the form of a base with a mushroom-shaped button on top is placed on the two brackets and tied thereto by wires being attached to the bottom of the base and holding the ligating element against the brackets to retain the arch wire in the grooves while the button permits fastening of an elastic band. Since the arch wire is retained on each tooth of a row of teeth by means of such ligating member or element anchoring facilities for stringing elastic bands between any two teeth are immediately available, and the placement of these elastic bands can be changed at will as the treatment requires without encountering any new problem as to fastening.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a perspective view of several teeth of a person each tooth being fitted with a band;

FIG. 2 is a section view along line 2—2 in FIG. 1 but on an enlarged scale showing also a ligating element in side view and about to be placed in fastened position;

FIG. 3 is an enlarged view of a portion of FIG. 1 but with the ligating element in place.

FIG. 4 is a side and section view as indicated by line 4—4 in FIG. 3;

FIG. 5 is a front view of the same portion shown in FIG. 3, and

FIG. 6 is a perspective, back view of the ligating element.

Proceeding now to the detailed description of the drawings. FIG. 1 illustrates teeth 10 which have been prepared for orthodontics. In particular, metal bands 11 have been fitted around each of the teeth as is conventional. Each band is provided on its front with two brackets 12 and 12a, one of them being shown in side view in FIG. 2. Each bracket is of T-shaped configuration, its stem 16 being welded to the band 11.

The wing portions 13 and 14 of the T's are of slightly downwardly drooping configuration. The brackets 12, 12a each have, in addition, a center groove 15. The two brackets 12 and 12a are so placed on band 11 that the respective grooves 15 are aligned. For purposes of orthodontic treatment, an arch wire 20 is placed into the grooves 15. Of course, other teeth have been fitted with bands such as 11 each carrying a pair of brackets such as 12, 12a. The arch wire 20 is placed in all the respective grooves. It can readily be seen that the arch wire is positively held by the two brackets as to the direction of its extension and therefore as to its orientation in relation to each band and tooth.

The arch wire 20 is fastened to the respective tooth, band and brackets as follows. A ligating element 30 is provided, being shown individually in FIGS. 2 and 6 prior to its use. The element 30 has a flat base 31 being integral on its top (which will be the front after attaching it to the band) with a holder or hook being a mushroom-shaped button 32 having a stem 33. The particular contour of this holder 32 is not essential except that it must be capable of holding the loop of an elastic band. Moreover, its outwardly projecting portion should be smooth so that skin tissue of the mouth may not be irritated on contact.

A wire loop is attached to the bottom of plate 31, e.g. being spot-welded thereto and forming a short loop 35 on one side of and at one end of base 31. The wire has two relatively long free ends 36 and 37 extending from the other end of base 31 for tying manipulation to be described below.

The several figures show the ligating element 30 on a considerably enlarged scale. By way of example, the length of the plate or base 31 may be about 3.5 mm, its width a little over 2 mm, and the height of the holder or button 32 may be a little over 1 mm. The ends of the plate 3 are slightly curved. Elements 30 can be made of stainless steel or of a plastic which is FDA approved for oral appliances.

For holding the arch wire 20 in place and for providing selective facilities for elastic band attachment, the ligating element 30 is placed on top of the two brackets 12 and 12a whereby the wires to the extent they are attached to the bottom of plate 31 enter the grooves 15 (see FIG. 2). The grooves 15 are deeper than the diameter of the arch wire. The loop 35 is bent down on the arch wire, and the free ends 36 and 37 are respectively run under the wing portions of the bracket 12, doubled back and run under the wing portions of bracket 12a and twisted tight to force the top of loop 35 down onto the arch wire. This way, the arch wire 20 is now fastened to the band 11 and to the tooth enveloped by that band. On the other hand, the holding or ligating element 30 is itself firmly attached to the tooth and an elastic band 40 may be looped around its button 32 (stem 33) and the corresponding button on the holder of another tooth. The respective stems are, thus, very suitable anchoring posts for the elastic band, and the buttons retain the elastic band and prevent its slipping off.

Usually, a large number of teeth are fitted with such bands and brackets to hold an arch wire 20 as it extends across an entire row of teeth. In each instance, a ligating element 30 is provided but not all buttons are used for attaching or anchoring elastic element such as a rubber band 40. However, all teeth fitted with bands carry a ligating element so that from time to time the placement of elastic band can be changed without having to provide for new holding facilities in each instance of change.

The invention is not limited to the embodiments described above but all changes and modifications thereof not constituting departures from the spirit and scope of the invention are intended to be included.

I claim:

1. An orthodontic appliance for use in combination with an orthodontic arch wire and an elastic band and including a band fitted around a tooth comprising in combination:
   a pair of T-shaped brackets on the band each having a groove on top, the grooves being aligned with each other and receiving the arch wire;
   a ligating member having a base placed on top of the grooves and retaining the arch wire therein, there being wire ends secured to the base and tied under the T-shaped brackets and twisted together to hold the member on the brackets; and
   the member having a hook on top of the base as anchoring post for a loop of the elastic band.

2. An appliance as in claim 1, said wires forming a loop secured to the bottom of the plate and extending generally in the direction of the arch wire as the plate is in position on the brackets, a loop projecting from one end of the base, the wire ends for being twisted on top of the arch wire.

3. An appliance as in claim 1, said grooves being of rectangular cross-section and the arch wire being round.

4. An appliance as in claim 1, said hook being a mushroom-shaped button.

* * * * *